US008476081B2

(12) United States Patent
Kranz et al.

(10) Patent No.: US 8,476,081 B2
(45) Date of Patent: Jul. 2, 2013

(54) ASSAY FOR EVALUATING AFFINITY AND SPECIFICITY OF LIGAND-ALBUMIN BINDING

(75) Inventors: James K. Kranz, Pottstown, PA (US); Gabrielle C. Todd, Ann Arbor, MI (US); Matthew J. Todd, Downingtown, PA (US)

(73) Assignee: Janssen Pharmaceutica NV, Beerse (BE)

( * ) Notice: Subject to any disclaimer, the term of this patent is extended or adjusted under 35 U.S.C. 154(b) by 299 days.

(21) Appl. No.: 12/885,865

(22) Filed: Sep. 20, 2010

(65) Prior Publication Data

US 2011/0124120 A1 May 26, 2011

Related U.S. Application Data

(60) Provisional application No. 61/244,166, filed on Sep. 21, 2009.

(51) Int. Cl.
*G01N 33/566* (2006.01)
(52) U.S. Cl.
CPC .................................. *G01N 33/566* (2013.01)
USPC ......... 436/501; 435/7.92; 435/7.93; 436/164; 436/172
(58) Field of Classification Search
None
See application file for complete search history.

(56) References Cited

U.S. PATENT DOCUMENTS

| | | | |
|---|---|---|---|
| 6,020,141 | A | 2/2000 | Pantoliano et al. |
| 6,036,920 | A | 3/2000 | Pantoliano et al. |
| 6,214,293 | B1 | 4/2001 | Pantoliano et al. |
| 6,232,085 | B1 | 5/2001 | Pantoliano et al. |
| 6,268,158 | B1 | 7/2001 | Pantoliano et al. |
| 6,268,218 | B1 | 7/2001 | Pantoliano et al. |
| 6,291,191 | B1 | 9/2001 | Pantoliano et al. |
| 6,303,322 | B1 | 10/2001 | Pantoliano et al. |

OTHER PUBLICATIONS

Colmenarejo, G. "In Silico Prediction of Drug-Binding Strengths to Human Serum Album", *Medicinal Research Reviews*, vol. 23, No. 3, pp. 275-301, (2003), Wiley Periodicals, Inc.

Epps, D.E. et al. "A General, Wide-Range Spectrofluorometric Method for Measuring the Site-Specific Affinities of Drugs toward Human Serum Albumin", *Analytical Biochemistry*, vol. 227, pp. 342-350, (1995).
Kragh-Hansen, U. et al. "Practical Aspects of the Ligand-Binding and Enzymatic Properties of Human Serum Albumin", *Biol. Pharm. Bulletin*, vol. 25 (6), pp. 695-704, (2002).
Mathias, U. et al. "Determination of Drug-Serum Protein Interactions via Fluorescence Polarization Measurements", *Anal. Bioanal. Chemistry*, vol. 388, pp. 1147-1156 (2007).
Matulis, D. et al. "Thermodynamic Stability of Carbonic Anhydrase: Measurements of Binding Affinity and Stoichiometry Using ThermoFluor", *Biochemistry*, vol. 44, pp. 5258-5266, (2005).
Sudlow, G. et al. "The Characterization of Two Specific Drug Binding Sites on Human Serum Albumin", *Molecular Pharmacology*, vol. 11, pp. 824-832 (1975).
Carter, et al, "Structure of Serum Albumin," *Advances in Protein Chemistry*, 1994; 45:152-203.
Pantoliano, et al., "High-Density Miniaturized Thermal Shift Assays as a General Strategy for Drug Discovery," *Journal of Biomolecular Screening*, 2001; 6:429-440.
Lam, K.S., "Application of Combinatorial Library Methods in Cancer Research and Drug Discovery," *Anticancer Drug Design*, 1997; 12:145-167.
Privalov, P.L., "Stability of Proteins: Small Globular Proteins," *Advances in Protein Chemistry*, 1979; 33:167-241.
Cohn, et al., "Preparation and Properties of Serum and Plasma Proteins. XIII. Crystallization of Serum Albumins from Ethanol-Water Mixtures," *Journal of the American Chemical Society*, 1947; 69:1753-1761.
Angelakou, et al., "A Displacement Approach for Competitive Drug-Protein Binding Studies Using the Potentiometric 1-anilino-8-naphthalene-sulfonate Probe Technique," *European Journal of Pharmaceutical Sciences*, 1999; 9:123-130.
Chamouard, et al. "Diclofenac Binding to Albumin and Lipoproteins in Human Serum," *Biochemical Pharmacology*,1985; 34 (10): 1695-1700.
Muller, et al., "Binding Sites of Fluorescent Probes on Human Serum Albumin," *Journal of Pharmacy and Pharmacology*, 1994; 46:300-304.
Furst, et al., "HPLC Analysis of Free Amino Acids in Biological Material—An Appraisal of Four Pre-Column Derivatization Methods," *Journal of Liquid Chromatography*, 1989; 12 (14): 2733-2760.

*Primary Examiner* — Gary W Counts
(74) *Attorney, Agent, or Firm* — Rajiv S. Shah

(57) ABSTRACT

A method for identifying a ligand or compound which binds to albumin comprises the steps of contacting a reaction mixture comprising a site-specific probe and albumin in the presence and the absence of the ligand or compound and measuring either dissociation constant $K_D$, inhibitor concentration $IC_{50}$ or fluorescence displacement; whereby a change in $K_D$, $IC_{50}$ and/or fluorescence in the presence of the ligand or compound is indicative of the ligand or compound binds to albumin.

10 Claims, No Drawings

ASSAY FOR EVALUATING AFFINITY AND SPECIFICITY OF LIGAND-ALBUMIN BINDING

CROSS REFERENCE TO RELATED APPLICATIONS

This application claims benefit of U.S. Provisional Patent Application Ser. No. 61/244,166, filed Sep. 21, 2009, which is incorporated herein by reference in its entirety and for all purposes.

BACKGROUND OF THE INVENTION

1. Field of the Invention

A method is provided for simultaneously detecting affinity and specificity of a ligand or compound to serum protein albumin by using a thermal shift assay and a site-specific competition assay.

2. Description of the Related Art

Albumin is an abundant plasma protein, accounting for about 60% of total proteins in plasma. One of the main physiological functions of albumin is the transport of non-esterified fatty acids in the circulatory system. Albumin is also a general transporter protein for various endogenous ligands, including metal ions, bilirubin, bile salts, tryptophan, hormones, and vitamins. In addition, albumin binds to a wide range of therapeutic drugs or compounds (review in Kragh-Hansen et al., Biol Pharm Bull 25: 695-704, 2002).

As therapeutic drugs bind to albumin in plasma and reach the target tissues in a bound form, the binding or affinity to albumin greatly affects the pharmacological properties of therapeutic drugs in plasma. For example, the binding to albumin reduces the concentration of free active therapeutic drugs in plasma. Alternatively, the binding to albumin promotes the solubilization of hydrophobic compounds, buffers the distribution of drugs through the body, and reduces metabolic clearance of drugs. Therefore, albumin is routinely used to screen and characterize potential candidate compounds from the early phase of drug discovery to the optimization process in medicinal chemistry (reviewed in Colmenarejo, Med Res Rev 23: 275-301, 2003; Kragh-Hansen et al., Biol Pharm Bull 25: 695-704, 2002).

Albumins of different species share highly conserved sequences, structures, and properties. Human serum albumin (HSA) is a protein with a monomeric molecular weight of about 67 kDa. Crystallographic studies have indicated that HSA has three domains I, II, and III, and two sub-domains A and B within each of the domains (Carter and Ho, Adv Protein Chem 45: 152-203, 1994). Competitive binding studies have shown that HSA has two primary binding sites I and II, and several secondary binding sites (Sudlow et al., Mol Pharmaco 11: 824-832, 1975). The binding site I, located at subdomain IIA, is larger and more flexible than the binding site II located at subdomain IIIA. The drugs or ligands have affinity to site I are mostly bulky heterocyclic anions, and the drugs or ligands have affinity to site II are mainly aromatic carboxylates. Subsequent studies show that endogenous ligands also have affinity to sites I and/or II (Kragh-Hansen et al., Biol Pharm Bull 25: 695-704, 2002; Curry et al., Biochimi Biophys Acta 1441: 131-140, 1990). Additionally, the binding of one ligand or compound at one site may affect the binding at other sites.

Several methods such as equilibrium dialysis, probe displacement, ultracentrifugation, and thermal shift assay have been used to detect formation of a ligand-albumin complex. These conventional methods analyze either the affinity or the specificity. To characterize both affinity and specificity properties of ligand-albumin binding, additional procedures, longer process time, more reagents and equipment, higher cost are required.

ThermoFluor® is a newly developed system for rapid thermal shift assay as described in Pantoliano et al. (J Biomol Screen 6: 429-440, 2001); Matulis et al. (Biochemistry 44: 5258-5266, 2005); U.S. Pat. Nos. 6,020,141; 6,036,920; 6,214,293; 6,232,085; 6,268,158; 6,268,218; 6,291,191; and 6,303,322; all of which are incorporated herein by reference in their entireties. Briefly, ThermoFluor® uses a fluorescent probe 1-anilinonaphtalene-8-sulfonate (1,8-ANS) to evaluate the binding affinity of ligands to a protein, independent of its biological function and activity. ThermoFluor® has not been applied to analyze ligand-albumin binding, and its existing condition may not be optimal for analyzing both specificity and affinity. For example, one condition disclosed in U.S. Pat. No. 6,020,141 utilizes about 100 µM of 1,8-ANS. This concentration may not be desirable for simultaneous analysis of specificity and affinity, as specificity analysis generally uses a fluorescent probe present in a less saturated range for a displacement assay to determine an accurate dissociation constant.

Thus, it is the objective of the present application to provide an efficient method for simultaneous analysis of both affinity and specificity of ligand-albumin binding in a high-throughput format.

SUMMARY OF THE INVENTION

An object of the present application is to provide a method for identifying a ligand which binds to albumin. The method comprises the steps of contacting a reaction mixture comprising a site-specific fluorescence probe and albumin in the presence and the absence of the ligand and measuring the level of fluorescence; whereby a change in the level of fluorescence in the presence of the ligand is indicative of the ligand binds to albumin.

Another object of the present application is to provide a method for determining a ligand-albumin interaction. The method comprises the steps of contacting a reaction mixture comprising a site-specific probe and albumin, measuring dissociation constant $K_D$ and inhibitor concentration $IC_{50}$, and comparing the value of $K_D$ and $IC_{50}$ to determine whether the ligand binds to albumin.

According to the present application, the probe may be 1,8-ANS, dansyl-sarcosine and iophenoxate. Also according to the present application, albumin may be human serum albumin, bovine serum albumin, rat serum albumin and mouse serum albumin. Further according to the present application, the reaction mixture may be monitored by a plate-based reader or a ThermoFluo® system.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

In one embodiment, the present invention comprises a method for determining both the affinity and specificity of a ligand which binds to albumin in a single assay, comprising the steps of the following:

a.) contacting a reaction mixture comprising a site-specific fluorescent probe and albumin in the presence and separately in the absence of a ligand; wherein the site-specific fluorescent probe:

i) increases in fluorescence, as measured by a spectral reading device, when bound to albumin;

ii) binds specifically to a binding site I or a binding site II on albumin; and iii) has a higher affinity for albumin in the denatured state than when albumin is in its native state;

and wherein ligand binding to binding site I or binding site II is measured by displacement of the site-specific fluorescent probe by the ligand when it binds to albumin;

b.) measuring an initial level of fluorescence for the reaction mixture in the presence and separately in the absence of the ligand;

c.) comparing the initial level of fluorescence for the reaction mixture in the presence and the absence of the ligand; whereby differences in the level of the initial fluorescence in the presence and the absence of the ligand indicates that the ligand does or does not bind to binding site I or binding site II on albumin;

d.) heating the reaction mixture;

e.) measuring a change in fluorescence of the reaction mixture associated with the thermal unfolding of albumin resulting from heating in the presence and separately in the absence of the ligand;

f.) generating a thermal unfolding curve from the change of fluorescence measured in (e) for albumin in the presence and separately in the absence of the ligand as a function of temperature for the reaction mixture;

g.) comparing the thermal unfolding curves for albumin in the presence and the absence of the ligand generated in (f); whereby differences in the thermal unfolding curves are used to determine the affinity of the ligand which binds to albumin; and h.) determining both the affinity and specificity of a ligand which binds to albumin by comparing the differences in the thermal unfolding curves in (g) and comparing the differences in the level of the initial fluorescence in (c); thereby determining both the affinity and specificity of a ligand which binds to albumin in a single assay.

In a second embodiment, the present invention comprises the method described above, wherein the initial level of fluorescence in step (b) and the change in fluorescence of the reaction mixture associated with the thermal unfolding in step (d) are measured by a plate-based fluorescence reader.

In a third embodiment, the present invention comprises the method described above, wherein albumin is human serum albumin, bovine serum albumin, rat serum albumin or mouse serum albumin.

In a fourth embodiment, the present invention comprises the method described above, wherein the site-specific fluorescent probe is 1-anilinonaphtalene-8-sulfonate (1,8-ANS) or dansyl-sarcosine.

In a fifth embodiment, the present invention comprises the method described above, wherein the site-specific fluorescent probe is 1,8-ANS.

In a sixth embodiment, the present invention comprises the method described above, wherein the site-specific fluorescent probe is dansyl-sarcosine.

In a seventh embodiment, the present invention comprises the method described above, wherein a change in the initial level of fluorescence of 1,8-ANS indicates that the ligand binds to albumin at binding site I.

In an eighth embodiment, the present invention comprises the method described above, wherein a change in the initial level of fluorescence of dansyl-sarcosine indicates that the ligand binds to albumin at binding site II.

DETAILED DESCRIPTION OF THE PRESENTLY PREFERRED EMBODIMENTS

The present application provides a method that overcomes the limitations of existing assays for ligand-albumin binding. The present method utilizes a thermal shift assay in combination with a site-specific competition assay for simultaneous analysis of affinity and specificity of ligand-albumin binding. The method provides a thermal shift reaction mixture, comprising a site-specific probe, albumin, and buffer.

A thermal shift or thermal stability assay measures a change in a biophysical parameter of a protein such as albumin over increasing temperature. The biophysical parameters may be measured by hydrodynamics, thermodynamics, calorimetry, and various spectroscopic techniques, and the results may be represented by a thermal denaturation curve. The preferred thermal shift assay is ThermoFluor® which is described in U.S. Pat. Nos. 6,020,141; 6,036,920; 6,214,293; 6,232,085; 6,268,158; 6,268,218; 6,291,191; and 6,303,322; all of which are incorporated herein by reference in their entireties.

ThermoFluor® evaluates the thermodynamic equilibrium of a protein between the folded/native state and the unfolded/denatured state, independent of the protein function, using a fluorescent molecule or probe. The fluorescent molecule emits lower fluorescence signal in an aqueous environment, such as a reaction or sample solution, than a hydrophobic environment, such as the interior of a protein. Since the fluorescent probe has higher affinity to hydrophobic amino acid residues which are usually embedded inside of the folded/native protein, the binding of the fluorescent probe to a denatured/unfolded protein generally results in a significantly higher levels of fluorescent signal. Therefore, ThermoFluor® detects a significantly higher fluorescence in the presence of the unfolded/denatured protein when the temperature increases to near or at the characteristic temperature.

A site-specific probe may be any molecule which binds to albumin. Preferably, the site-specific probe is a fluorescent molecule compatible with ThermoFluor®. The preferred site-specific probe includes but is not limited to 1,8-ANS, 2,6-TNS, DAPDXYL® derivatives or dansyl derivatives. The site-specific probe may have affinity to either binding site I or II of albumin. The preferred site-specific probe for the site I is 1,8-ANS and the preferred site-specific probe for the site II is dansyl-sarcosine.

It is found herein that the site-specific probe may not be present in any concentration or range. The site-specific probe needs to be minimized such that the probe may be readily displaced by a test ligand or compound, such that the dissociation constant ($K_D$) of the test ligand measured in the presence of the site-specific probe is similar to those measured in the absence of the probe. According to the finding of the present application, the concentration of the site-specific probe such as 1,8-ANS may range from about 0.5 µM to about 20 µM, preferably from about 1 µM to about 8 µM, and most preferably from about 2 µM to about 4 µM. The appropriate amount of probe may vary depending on the type of probe, albumin, buffer system, or the assay condition.

In one embodiment, the ligand-albumin binding is analyzed using the thermal shift assay ThermoFluor and the site specific probe 1,8-ANS. Since 1,8-ANS binds to the unfolded/native albumin at the site I, ThermoFluor® may detect a higher fluorescence from 1,8-ANS bound to the native/unfolded albumin and the fluorescence is subsequently reduced upon denaturing/unfolding of albumin and dissociation of 1,8-ANS. In addition, the dose-dependent displacement of 1,8-ANS with increasing concentrations of a ligand may be used to localize the binding site or specificity of the compound. Therefore, the fluorescence signal of 1,8-ANS may be used to simultaneously detect the affinity of the ligand in a thermal shift assay such as ThermoFluor® and the specificity of the ligand by displacement or lack of displacement of 1,8-ANS on the site I of albumin by a test ligand/compound.

Albumin from various species may be used for the assay of the present application. Suitable albumins may include but not limited to proalbumins, alphafetoprotein albumins, alpha-albumins, lactalbumins, and ovalbumins which may be derived from human, bovine, canine, cavia porcellus, chicken, cobra, donkey, eel, equine, feline, frog (*x. laevis, r. catesbeiana, r. shgiperica*), gerbil, goat, hamster, lamprey, lungfish, primates (macaque gorilla, chimpanzee, orangutan, rhesus monkey), mouse, pig, rabbit, rat, salamander, salmon (alb1 & alb2), sheep, turkey and zebrafish. Naturally occurring human albumin nucleotide polymorphisms (alloalbumins) or variant thereof may also be used. Human serum albumin (accession number NM 000477.4), bovine serum albumin (accession number NM 190992.2), rat serum albumin (accession number NM 134326.2), and mouse serum albumin (accession number NM 009654) are preferred.

Albumin may be obtained from a commercial source or produced by recombinant DNA technology, isolated or purified from cells by any method commonly known in the art. The purified or isolated albumin may be associated with endogenous ligands such as lipids, amino acids, metabolites and the like. Additional procedures may be used to remove these ligands as they may affect the subsequent analysis. The apo or unliganded state of albumin is preferred for the method of the present application. When apo albumin is generated, the purify of the albumin in the total protein extract ranges from about 80% to about 100%, preferably from about 90% to 100%, and most preferably from about 97% to about 100%.

Albumin may be present in any desired concentration or range. The concentration may range from about 0.01 µM to about 500 µM, preferably from about 0.1 µM to about 50 µM, more preferably from about 0.5 µM to about 5 µM and most preferably from about 1 µM to about 2 µM. The appropriate amount of albumin may be varied depending on test ligand, other component or condition of the assay.

In addition to the site-specific probe and albumin, the reaction mixture may include a buffering system where the pH is about 7.2. A suitable buffer system may include TBS, PBS, MOPS, MES, CHAPSO, PIPES, HEPES, borate salt or sodium phosphate. Other buffer systems commonly known to a person skilled in the art may also be used. A PIPES buffer system is preferred.

A variety of other reagents may also be optionally included in the reaction mixture. These include reagents such as salts, detergents, metals, fatty acids, other endogenous ligands, and the like that may be used to facilitate detection of albumin binding. Such reagents may also reduce non-specific or background interactions of the reaction components. Other reagents that improve the efficiency of the assay such as inhibitors, antimicrobial agents and the like may also be used.

In one embodiment, a 1× reaction mixture having about 25 mM PIPES at pH 7.2, about 0.15 M NaCl, and about 0.002% Tween®-20 (polysorbate 20) is provided. Prior to the reaction, human serum albumin and the site-specific probe of 1,8-ANS are added into 1× reaction buffer. The resulting reaction mixture comprises a final concentration of about 50 µg/mL of human serum albumin and about 4 µM of 1,8-ANS in 1×PIPES buffer.

As used herein, the terms "ligand", "test ligand" or the like refer to any substance to be analyzed for albumin binding. A ligand may be determined using the present method includes but not limited to peptide, protein such as enzymes and antibodies, drugs, compounds, or small molecules. By way of example, the present method is used for determining and analyzing compounds or compound libraries.

Compounds encompass numerous chemical classes, although typically they are organic compounds. Also, compounds comprise functional chemical groups necessary for structural interactions with polypeptides, and typically include at least an amine, carbonyl, hydroxyl or carboxyl group, preferably at least two of the functional chemical groups and more preferably at least three of the functional chemical groups. Compounds can comprise cyclic carbon or heterocyclic structure and/or aromatic or polyaromatic structures substituted with one or more of the above-identified functional groups. Compounds also can be biomolecules such as peptides, saccharides, fatty acids, sterols, isoprenoids, purines, pyrimidines, derivatives or structure analogs of the above, or combinations thereof and the like. Where the compound is a nucleic acid, the compound typically is a DNA or RNA molecule, although modified nucleic acids having non-natural bonds or subunits are also contemplated.

Compounds may be obtained from a wide variety of sources including libraries of synthetic or natural compounds. For example, numerous means are available for random and direct synthesis of a wide variety of organic compounds and biomolecules, including expression of randomized oligonucleotides, synthetic organic combinatorial libraries, phage display libraries of random peptides, and the like. Compounds can also be obtained using any of the numerous approaches in combinatorial library methods known in the art, including: biological libraries; spatially addressable parallel solid phase or solution phase libraries: synthetic library methods requiring deconvolution; the "one-bead one-compound" library method; and synthetic library methods using affinity chromatography selection (Lam, 1997, Anticancer Drug Des. 12:145). Alternatively, libraries of natural compounds in the form of bacterial, fungal, plant and animal extracts are available or readily produced. Additionally, natural and synthetically produced libraries and compounds can be readily modified through conventional chemical, physical, and biochemical means.

Further, known pharmacological agents may be subjected to directed or random chemical modifications such as acylation, alkylation, esterification, amidification, etc. to produce structural analogs of the agents. Compounds can be selected randomly or can be based on existing compounds that bind to albumin. Therefore, a source of candidate agents is libraries of molecules based on the known compounds that bind to albumin, in which the structure of the compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries based on the existing albumin-binding compound.

The ligand or compound may be solubilized in any solution compatible with albumin and site-specific probe, and suitable for ThermoFluor®. A suitable solution includes but is not limited to DMSO, water, ethanol, methanol, acetonitrile, or mixture thereof. DMSO is preferred.

The test ligand or compound may be present in any concentration suitable for analyzing the binding to albumin. Preferably, the concentration of the ligand is in excess of the concentration of albumin. The concentration of the ligand may range from about 0.001 μM to about 100,000 μM, preferably from about 0.01 μM to about 1,000 μM, and most preferably from about 0.1 μM to about 250 μM.

The reaction mixture and the ligand may be dispensed into a container commonly used in the laboratory. The container such as a tube or a plate may be made with any material in any shape or form suitable for albumin binding analysis and thermal shift assay. For example, the container may be a single or plurality of wells. The reaction mixture and the ligand may be dispensed into the container in any order or format. For example, the ligand may be dispensed to the container prior or subsequent to the addition of the reaction mixture comprising the site-specific probe, albumin, and buffer. The ligand and the reaction mixture may also be dispensed simultaneously. Further, the reaction mixture and the ligand may also be mixed in a first container then dispensed into a second container. The reaction mixture and/or the ligand may be dispensed using a multichannel dispensing system, such as Hummingbird™, LabCyte Echo® or the like.

By way of example, the volume of test ligand or compound may range from about 0.001 to 1,000 μL, preferably from about 0.005 to 5 μL, and most preferably from about 0.001 to 1 μL. The volume of the reaction mixture may range from about 0.01 μL to about 1,000 μL, preferably from about 1.5 μL to 10 μL, and most preferably from about 2.0 μL to about 3 μL. Total volume of a sample of the ligand-albumin assay may range from about 0.01 to about 1,000 μL, preferably from about 0.1 to about 25 μL, more preferably from about 0.5 to about 10 μL, and most preferably from about 1 μL to about 5 μL. In one embodiment, the ligand may be present in the volume of about 0.05 μL and the reaction mixture may be present in about 2.4 μL, and the total volume of the sample is about 2.45 μL.

Prior to the initiation of the albumin binding assay, an inert solvent may be added to cover the sample to prevent evaporation during heating process. A suitable inert solvent may include silicone oil, mineral oil, or the like. Silicone oil is preferred. The volume of silicone oil may range from about 0.005 to 500 μL, preferably from about 0.05 to about 25 μL, and most preferably from about 0.8 μL to about 1.2 μL is the working range.

The above described assay may be used in a high throughput format for screening compounds or compound libraries, identifying candidate compounds which bind to albumin, and evaluating their equilibrium binding. The term "high throughput" refers to an assay design that allows easy screening of multiple samples simultaneously and capacity for robotic manipulation. Another desired feature of high throughput assays is an assay design that is optimized to reduce reagent usage or minimize the number of manipulations in order to achieve the analysis desired. Examples of assay formats include micro-titer plates such as 96-well or 384-well plates, levitating droplets, and "lab on a chip" microchannel chips used for liquid handling experiments. It is well known in the art that as miniaturization of plastic molds and liquid handling devices are advanced, or as improved assay devices are designed, greater numbers of samples may be performed using the method of the present application.

According to the present method, the reaction mixture comprising the site-specific probe, albumin and buffer is contacted with a ligand in a container. The container is heated over a range of temperatures, in an interval or a continuous mode, by a heating element. In another example, the reaction mixture comprising the site-specific probe, albumin and buffer is contacted with a plurality of test ligands in each container or well of a 96- or 384-microtiter plate. The wells of the plate are simultaneously heated over a range of temperatures by a heating element in an interval or a continuous mode.

The heating element may be any element capable of heating samples rapidly and reproducibly. The samples may be heated on a single heating element. The samples may also be heated to a given temperature on one heating element then moved to another heating element to be heated to another temperature. Heating can be accomplished in regular or irregular intervals. To generate a smooth denaturation curve, the samples are heated evenly, preferably in intervals of about 1° C. or about 2° C. The samples may be heated across a range of temperature; for example, from about 10° C. to about 150° C. and preferably from about 25° C. to about 110° C.

While heating, the fluorescence signal from the samples may be measured. The samples may be heated and measured by the spectral reading device in a continuous mode. Preferably, the samples are heated continuously and spectral readings are measured while the samples are being heated. The samples may be measured simultaneously, individually, or in group of groups of at least two at a time.

The spectral device consists of a scanner and a control software system. The system is capable of quantifying soluble fluorescence emission. Fluorescence emission or signal may be detected by a Charged Coupled Device (CCD) camera. Other similar device may be used to detect the fluorescence signal.

The term "contacting" refers broadly to placing albumin in solution with the ligand to be analyzed for binding, such as turning, swirling, shaking or vibrating of a reaction mixture comprising albumin and the ligand. More specifically, contacting refers to the mixing of the reaction mixture comprising albumin with the ligand. Mixing may be accomplished by repeated uptake and discharge through a pipette tip. Preferably, contacting refers to the equilibration of binding between albumin and the ligand. Contacting may occur in the container or before albumin and the ligand are placed in the container.

The terms "sample", "sample reaction" or variants thereof refer to the reaction in a container having the reaction mixture and a test ligand or compound and the terms "control sample", "control reaction" or variants thereof refer to the reaction in a container having only the reaction mixture, i.e. in the absence of a test ligand or compound.

As used herein, the terms 'significantly higher', 'significantly lower' and 'significantly different', as used herein, refer to the difference would lead a person skilled in the art to believe that the fluorescence signal is changed. The difference in the fluorescence signal may be at least 10 fold in comparison with the standard deviation of the background signal.

The terms "protein denatures", "denatured protein", "unfolded protein", "non-native protein", or variant thereof refer to a protein which has been treated to remove or disrupt secondary, tertiary, or quaternary structure. The terms "native protein", "folded protein", "non-denatured protein", or variant thereof refer to a protein which possesses the degree of secondary, tertiary or quaternary structure that provides the protein with full chemical and biological function. A native protein is one which has not been heated and has not been treated with denaturation agents or chemicals such as urea. Also, the terms "folding" "refolding", "renaturing", or variants thereof refer to the acquisition of the correct secondary, tertiary, or quaternary structure, of a protein or a nucleic acid, which affords the full chemical and biological function of the biomolecule.

Equations relevant to analysis of thermal shift assays have been described previously, for example, Matulis et al., Biochemistry 13, 5258-66, 2005. A thermal stability assay measures the temperature-induced change in equilibrium position between the folded or native state (N) and the denatured or unfolded state (U); a thermal shift assay measures the additional stabilization of the native state induced by a ligand (L) binding to the native protein as set forth in Equations 1 to 4.

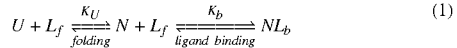
(1)

$$\Delta G(T) = \Delta G_U(T) + \Delta G_b(T) \quad (2)$$

$$K_U = \frac{[U]}{[N]} = e^{-(\Delta G_U(T))/RT} \quad (3)$$

$$K_b = \frac{[NL_b]}{[N][L_f]} = e^{-(\Delta G_b(T))/RT} \quad (4)$$

wherein $L_f$ is the concentration of free ligand, $L_b$ is the concentration of bound ligand, $K_b$ is ligand binding constant, $K_a$ is ligand association constant, $NL_b$ is the complex of native protein and bound ligand, $\Delta G(T)$ is the total stability of the ligand-protein complex as defined by the temperature-dependent free energy, which is a sum of the protein stability ($\Delta G_U(T)$) plus the binding energy ($\Delta G_b(T)$), $K_U$ is the equilibrium constant for the protein unfolding, $K_b$ is the equilibrium constant of the binding affinity, T is the temperature at any point over the range of the experiment in degrees of Celsius or Kelvin, and R is the universal gas constant in cal/mol*K.

Fluorescence signals may be collected as described above, from which a thermal denaturation curve may be determined by plotting the change in fluorescence signal as a function of temperature. The temperature midpoint, $T_m$, of a thermal denaturation curve is the characteristic temperature at which the concentration of N and U are equivalent. As the binding of compounds or ligands to albumin causes an increase in thermal stability of albumin, the midpoint of an unfolding transition or thermal denaturation curve will occur at a higher temperature. The difference between the $T_m$, in the absence of ligand and the presence is referred to as $\Delta T_m$. Since the contribution of binding energy to protein stability is determined by both the binding affinity and the ligand concentration, different ligand/compound binding may be compared based on the magnitude of $\Delta T_m$ at a fixed concentration of ligand/compound. Alternatively, a series of Tm gathered at widely varying ligand concentrations may be used to determine a Kd of the test ligand.

To measure the strength of ligand binding from a thermal shift assay, the data may be fit in two stages. These are described by below Equations 5 to 9.

$$y(T) = y_F + \frac{y_U - y_F}{1 + e^{\Delta G_U(T_m)/RT}} = y_U + \frac{y_F - y_U}{1 + e^{-\Delta G_U(T_m)/RT}} \quad (5)$$

$$y_F(T) = y_{F,T_m} + m_F(T - T_m) \quad (6)$$

$$y_U(T) = y_{U,T_m} + m_U(T - T_m) \quad (7)$$

$$\Delta G_U(T) = \Delta H_U(T) - T\Delta S_U(T) \quad (8a)$$

$$\Delta G_U(T) = \Delta H_{U,T_r} + \Delta C_{p,U}(T - T_r) - T(\Delta S_{U,T_r} + \Delta C_{p,U} \ln(T/T_r)) \quad (8b)$$

$$y(T) = y_{F,T_m} + m_F(T - T_m) + \quad (9)$$

$$\frac{y_{U,T_m} - y_{F,T_m} + m_U(T - T_m)}{1 + e^{\Delta H_{U,T_r} + \Delta C_{p,U}(T-T_r) - T(\Delta S_{U,T_r} + \Delta C_{p,U} \ln(T/T_r))/RT}}$$

First, the fluorescence in the thermal shift assay (y(T)) is fit to Equation 5 to determine the stability of albumin at each test concentration. Two terms in Equation 5 define the fluorescence of 1,8-ANS in the presence of fully folded albumin, $y_F(T)$, and fully unfolded albumin, $y_U(T)$. Both of these are linear functions as defined in Equations 6 and 7, wherein $y_{F,Tm}$ and $y_{U,Tm}$ are fluorescence intensities of 1,8-ANS in the presence of native and non-native protein referenced to the melting temperature $T_m$, and $m_F$ and $m_U$ are the linear temperature dependences of the fluorescence intensity plus native and non-native protein, respectively. The protein stability term $\Delta G_U(T)$ in Equation 5 is the same as defined in Equation 2, and may be replaced by the Gibbs-Helmholtz relationships, Equations 8a and 8b (P. L. Privalov, Adv Prot Chem 33: 167-241, 1979). Equation 8a shows that the temperature-dependent Gibbs free energy of protein unfolding, $\Delta G_U(T)$, is comprised of a temperature-dependent enthalpy, $\Delta H_U(T)$, and a temperature-dependent entropy, $\Delta S_U(T)$. These in turn have their temperature dependence (Equation 8b) described by a constant enthalpy, $\Delta H_{U,T_r}$, and entropy, $\Delta S_{U,T_r}$, at the reference temperature, $T_r$, set to the value of the unfolding $T_m$ of albumin in the absence of a ligand. In addition, a heat capacity for protein unfolding, $\Delta_U C_p$, defines the temperature dependence of $\Delta_U H_{T_r}$ and $\Delta_U S_{T_r}$. Equations 5 and 8b are combined into Equation 9, which is used in a non-linear least squares minimization algorithm to estimate parameters of $y_{F,Tm}$ and $m_F$, $y_{U,Tm}$ and $m_U$, $\Delta H_{U,T_r}$, and $T_m$ for each sample. The value of $\Delta_U C_p$ is held fixed.

In a second stage, the $T_m$ of albumin at each concentration of test ligand is related to the expected effect for a ligand with a given binding affinity, $K_b$, which is defined by Equations 10a and 10b. The relationship between total ligand concentration, total protein concentration, and the two equilibrium constants for protein unfolding and ligand binding is defined by Equation 10a.

$$L_t = (1 - K_U)\left(\frac{P_t}{2} + \frac{1}{K_U K_b}\right) \quad (10a)$$

$$L_t = \left(1 - e^{-(\Delta H_{U,T_r} + \Delta C_{p,U}(T_m - T_r) - T_m(\Delta S_{U,T_r} + \Delta C_{p,U} \ln(T_m/T_r)))/RT_m}\right) \times \quad (10b)$$

$$\left(\frac{\frac{P_t}{2} +}{1 / e^{-(\Delta H_{U,T_r} + \Delta C_{p,U}(T_m - T_r) - T_m(\Delta S_{U,T_r} + \Delta C_{p,U} \ln(T_m/T_r)))/RT_m} \times e^{-(\Delta H_b(T_0) + \Delta C_{p,b}(T - T_0) - T(\Delta S_b(T_0) + \Delta C_{p,b} \ln(T/T_0)))/RT}}\right)$$

wherein $P_t$ is the total protein concentration which is the sum of the concentrations of N, U, and $NL_b$, $L_t$ is the total ligand concentration which is the sum of concentrations of $L_f$ and $NL_b$ of Equation 1. Additionally, $K_U$ is described in terms of the temperature-dependent enthalpy, entropy, and heat capacity of protein unfolding in Equation 8b; and $K_b$ is described in terms of an enthalpy, $\Delta H_b(T_0)$, an entropy, $\Delta S_b(T_0)$, and heat capacity, $\Delta C_{p,b}$, of ligand binding in Equation 10b.

In addition to the thermal shift assay, the assay test plate may be utilized in a separate fluorescence measurement using a plate-based reader that is compatible with any relevant wavelengths. The preferred plate-based reader is Tecan Satire II. The displacement of site-specific probe such as 1,8-ANS from albumin site 1 by test ligand may cause a decrease in observed fluorescence that may be fit to Equation 11 to determine the value of $IC_{50}$.

$$y = y_{high} + \frac{y_o - y_{high}}{1 + ([I]/IC_{50})^h} \quad (11)$$

wherein y is the fluorescence at any inhibitor concentration [I], $y_o$ is the fluorescence at zero inhibitor concentration, $y_{high}$ is the fluorescence of fully displaced fluorescence probe, $IC_{50}$ is the inhibitor concentration that gives 50% change in fluorescence between $y_0$ and $y_{high}$ endpoints, and h is the Hill Coefficient. Additionally, the percent displacement may be determined by $(y-y_{high})$, divided by the difference of low $(y_0)$ and high endpoints $(y_{high})$, wherein y is determined at the second highest concentration.

The present method provides a method for simultaneous analysis of ligand-albumin binding properties, which may be categorized into at least five types. Type 1 refers to a ligand binding to site I, wherein the value of $K_D$ is similar to or within a range of about 4-fold of the value of $IC_{50}$ and percent displacement of fluorescence is more than about 20%, preferably about 50%, and most preferably about 70%. Type 2 refers to a ligand binding to site II, wherein the value of $K_D$ is at least 5-fold lower than the value of $IC_{50}$ and the percent displacement of fluorescence is less than about 20%. Type 3 refers to a ligand binding to both sites I and II, wherein the value of $K_D$ is at least 4-fold lower than the value of $IC_{50}$ and the percent displacement of fluorescence is more than about 30%, preferably about 50%, and most preferably about 70%. Type 4 refers to a ligand which has no or weak binding to either site I or II, wherein the values of $K_D$ and $IC_{50}$ may not be measurable within the tested concentrations of a ligand. Type 5 refers to a fluorescent compound, which has a dose-dependent increase of fluorescence, i.e. the percent displacement of fluorescence is more than about 100% or not determined, and an $IC_{50}$ may not be measurable even though $K_D$ may be determined.

All references described in this section and the Examples are incorporated herein by their entirety.

The invention is not limited by the embodiments described above which are presented as examples only but can be modified in various ways within the scope of protection defined by the appended patent claims.

Example 1

Human Serum Albumin (HSA), with the amino acid sequence of Accession number NM 000477.4, was purchased from Sigma (A-9511). Bovine Serum Albumin (BSA), with the amino acid sequence of Accession number NM 180992.2, was purchased from Sigma (A-7638). Rat Serum Albumin, with the amino acid sequence of Accession number NM 134326.2, was purchased from Sigma (A-6414). Mouse Serum Albumin, with the amino acid sequence of Accession number NM 009654, was purchased from Sigma (A-3559). The above albumins were prepared using method IV of Cohn et al. (J. Am. Chem. Soc. 69: 1753-1761, 1947) and purified with 1× crystallization. The purity of the albumins ranges from about 97% to about 99% as determined by agarose gel electrophoresis.

The fluorescent molecule of 1,8-ANS was purchased from Invitrogen (catalog number A-47). Silicone oil was purchased from Sigma (catalog number 85411).

The compounds, except Iodopanoate, were obtained from Sigma (Saint Louis, Mo.). Iodopanoate was obtained from TCI America (Portland, Oreg.).

1× reaction mixture of about 50 μg/mL human serum albumin, about 4 μM 1,8-ANS, about 150 mM NaCl, about 25 mM PIPES, pH 7.2, and about 0.002% Tween®-20 was prepared.

Unless otherwise noted, the materials used in the examples were obtained from readily available commercial suppliers or synthesized by standard methods known to one skilled in the art of chemical synthesis.

Example 2

A serial dilution of about 0.019625, 0.03925, 0.0785, 0.1565, 0.3125, 0.625, 1.25, 2.5, 5, 10, and 20 mM of warfarin or flurbiprofen in 100% DMSO was prepared. About 50 nLs of the compounds were dispensed into a black 384-well polypropylene microplate (Abgene: TF-0384/k) using a Hummingbird™ capillary liquid handling instrument (Genomics Solutions). Then about 4 μLs of 1× reaction mixture described in Example 1 was added into the plate so the final assay volume is about 4.05 μLs in each well. To prevent evaporation, about 1 μL of silicone oil was added to the plate using multichannel pipettors. The final concentration of warfarin or flurbiprofen in each sample was about 0.244, 0.488, 0.977, 1.95, 3.91, 7.81, 15.6, 31.3, 62.5, 125, or 250 μM.

The plates were loaded onto a ThermoFluor® device and heated from about 25° C. to about 95° C. at a ramp-rate of about 1° C. per minute. Fluorescence was measured by continuous illumination with UV light (Hamamatsu LC6) via fiber optic and filtered through a band-pass filter of about 390±10 nm; >6 OD cutoff. Fluorescence emissions were detected by measuring light intensity using a CCD camera (Sensys, Roper Scientific) filtered to detect about 500±25 nm; >6 OD cutoff. This allows for the entire plate to be simultaneously monitored and each sample to be independently monitored. One or more images were collected at an interval of every about 0.5° C. to about 1° C. The sum of the pixel intensity at a given area of the plate was recorded vs. temperature.

The denaturation curve of albumin in the presence of warfarin or flurbiprofen was determined from the change of fluorescence as a function of temperature. The values of $T_m$, $\Delta H$, $y_{F,Tm}$, $m_F$, $y_{U,Tm}$ and $m_U$ were calculated for each sample according to Equation 9. Further, the value of $T_m$ over the compound concentration was used to calculate the binding constant ($K_D$) using Equation 10b. A shift in the denaturation curve of albumin indicates whether the compound binds to albumin, and the value of $K_D$ indicates the binding strength of compounds to albumin. A shift of the fluorescence signal indicates the specificity of compounds to albumin, and the value of $IC_{50}$ indicates the binding strength to the site I (Equation 11). The results of warfarin or flurbiprofen binding to albumin were summarized in Table 1.

TABLE 1

The results of warfarin or flurbiprofen binding to albumin.

| | Warfarin | | Flurbiprofen | |
|---|---|---|---|---|
| Concentration (μM) | HSA $T_m$ (° C.) | Fluorescent Signal (%) | HSA $T_m$ (° C.) | Fluorescent Signal (%) |
| 0 | 74.3 | 100 | 74.0 | 100% |
| 0.244 | 74.4 | 106 | 74.4 | 110% |
| 0.488 | 74.1 | 87 | 74.1 | 105% |

TABLE 1-continued

The results of warfarin or flurbiprofen binding to albumin.

| | Warfarin | | Flurbiprofen | |
|---|---|---|---|---|
| Concentration (μM) | HSA $T_m$ (° C.) | Fluorescent Signal (%) | HSA $T_m$ (° C.) | Fluorescent Signal (%) |
| 0.977 | 74.2 | 100% | 74.3 | 102% |
| 1.95 | 74.0 | 84% | 74.4 | 104% |
| 3.91 | 74.2 | 82% | 75.0 | 118% |
| 7.81 | 74.3 | 77% | 75.1 | 106% |
| 15.6 | 74.7 | 76% | 75.7 | 111% |
| 31.3 | 75.0 | 67% | 76.1 | 108% |
| 62.5 | 75.6 | 67% | 76.8 | 101% |
| 125 | 76.1 | 63% | 78.2 | 109% |
| 250 | 76.7 | 58% | 80.2 | 105% |
| Result | $K_D$ = 11 μM | $IC_{50}$ = 20 μM | $K_D$ = 2.7 μM | $IC_{50}$ = N.D.[1] |

[1]Not determined.

The value of the initial fluorescence of 1,8-ANS bound to albumin in the presence of warfarin and flurbiprofen is shown in Table 1 at each concentration of compound; the fluorescence is normalized as a percentage of the fluorescence of in the absence of any compound. As shown in Table 1, the value of $T_m$ increased in the presence of warfarin and flurbiprofen and the value of $T_m$ was proportional with their affinity and concentrations. Additionally, a dose-dependent decrease in fluorescence with increasing compound concentration of warfarin. This indicates warfarin binds to site 1 of albumin which is consistent with previous report (Kragh-Hansen et al., Biol Pharm Bull 25: 695-704, 2002). In contrast, the fluorescence of 1,8-ANS is not decreased by flurbiprofen and is slightly increased. This result indicates flurbiprofen does not compete with 1,8-ANS and does not bind to site I. This is consistent with the previous report that flurbiprofen binds to site II of albumin.

Example 3

A stock solution of about 10 mM of warfarin, phenylbutazone, salicylate, indomethacin, tolbutamide, chlorpropamide, iophenoxate, sulfadimethoxine, sulfathiazole, furosemide, tenoxicam, valproate, quercetin, clofibrate, ketoprofen, iodopanoate, ibuprofen, s-naproxen, chlorothiazide, diclofenac, carprofen, norharmane, flurbiprofen, L-tryptophan, octanoate or indoxylsulfate was prepared in 100% DMSO. A serial dilution of about 0.00983125, 0.019625, 0.03925, 0.0785, 0.1565, 0.3125, 0.625, 1.25, 2.5, 5, and 10 mM were prepared from the stock solution. About 50 nLs of the above compounds were dispensed into a black 384-well polypropylene microplate (Abgene: TF-0384/k) using a Hummingbird™ capillary liquid handling instrument (Genomics Solutions). Then about 4 μLs of 1× reaction mixture described in Example 1 was added into the plate so the final assay volume is about 4.05 μLs in each well. The final concentration of the above compounds was about 0.244, 0.488, 0.977, 1.95, 3.91, 7.81, 15.6, 31.3, 62.5, 125, or 250 μM.

Additionally, a stock solution of about 5 mM canrenoate, bilirubin, or L-thyroxine was prepared in 100% DMSO. A serial dilution of about 0.00983125, 0.019625, 0.03925, 0.0785, 0.1565, 0.3125, 0.625, 1.25, 2.5, and 5 mM were prepared from the stock solution. About 50 nLs of the above compounds were dispensed into a black 384-well polypropylene microplate (Abgene: TF-0384/k) using a Hummingbird™ capillary liquid handling instrument (Genomics Solutions). Then about 4 μLs of 1× reaction mixture described in Example 1 was added into the plate so the final assay volume is about 4.05 μLs in each well. The final concentration of the above compounds was about 0.244, 0.488, 0.977, 1.95, 3.91, 7.81, 15.6, 31.3, 62.5, 125, or 250 μM. The final concentration of canrenoate, bilirubin, or L-thyroxine in each sample was about 0.244, 0.488, 0.977, 1.95, 3.91, 7.81, 15.6, 31.3, 62.5, or 125 μM.

The compounds and 1× reaction mixture were dispensed and measured for the fluorescence value using the plate-based reader Tecan® Safire II. Then the plate was heated in a ThermoFluor® system and measured for fluorescence value and the thermal shift value. The fluorescence values were measured twice by both plate reader and ThermoFluor®. The fluorescence value obtained from ThermoFluor® was used for qualitative assessment whereas those from the plate reader was used for quantitative assessment. The value of $IC_{50}$ was determined by the fluorescence obtained from the plate reader and was fit using Equation 11 described above. The value of $K_D$ was determined by the readings from ThermoFluor® and was fit using Equation 10b described above. The results were summarized in Table 2.

TABLE 2

The values of dissociation constant ($K_D$) and the displacement of the site-specific probe from the albumin binding assay with a panel of compounds.

| Test Ligand | [1]HSA - $K_D$ (μM) | [2]HSA - $IC_{50}$, μM (% Displacement) | Type of HSA Binding Interaction | Reported Binding Site |
|---|---|---|---|---|
| Warfarin | 9.4 | 22.2 (79) | Type 1 | Site 1 |
| Phenylbutazone | 14.0 | 50 (73) | Type 1 | Site 1 |
| Salicylate | N.D. | N.D. (20) | Type 4 | Site 1 |
| Indomethacin | 4.4 | N.D. (49) | Type 3 | Site 1 |
| Tolbutamide | 29.8 | N.D. (41) | Type 3 | Site 1 |
| Chlorpropamide | 82.0 | N.D. (20) | Type 4 | Site 1 |
| Iophenoxate[3] | 0.044 | 0.711 (129) | Type 1 | Site 1 |
| Sulfadimethoxine | N.D. | 96 (71) | Type 1 | Site 1 |
| Sulfathiazole | N.D. | N.D. (40) | Type 4 | Site 1 |
| Furosemide | 16.7 | N.D. (18) | Type 2 | Site 1 |
| Tenoxicam | 13.0 | 35.5 (84) | Type 1 | Site 1 |
| Valproate | N.D. | N.D. (31) | Type 4 | Site 1 |
| Canrenoate | N.D. | N.D. (33) | Type 4 | Site 1 |
| Quercetin | 7.9 | 25 (51) | Type 1 | Site 1 |
| Clofibrate | N.D. | N.D. (10) | Type 4 | Site 2 |
| Ketoprofen[4] | 21.7 | 135 (30) | Type 3 | Site 2 |
| Iodopanoate | 0.633 | 7.45 (83) | Type 3 | Site 2 |
| Ibuprofen | 5.3 | N.D. (33) | Type 3 | Site 2 |

TABLE 2-continued

The values of dissociation constant ($K_D$) and the displacement of the site-specific probe from the albumin binding assay with a panel of compounds.

| Test Ligand | [1]HSA - $K_D$ (μM) | [2]HSA - $IC_{50}$, μM (% Displacement) | Type of HSA Binding Interaction | Reported Binding Site |
|---|---|---|---|---|
| S-Naproxen | 5.9 | N.D. (02) | Type 2 | Site 2 |
| Chlorothiazide | N.D. | N.D. (12) | Type 4 | Site 2 |
| Diclofenac[4] | 2.6 | 44.5 (71) | Type 3 | Site 2 |
| Carprofen | 2.1 | 8.39 (87) | Type 3 | Site 2 |
| Norharmane | 17.6 | N.D. (N.D.) | Type 5 | Site 2 |
| Flurbiprofen | 2.1 | 154 (47) | Type 3 | Site 2 |
| Bilirubin | N.D. | N.D. (11) | Type 4 | Site 1 |
| Octanoate | N.D. | N.D. (00) | Type 4 | Multiple sites |
| L-Tryptophan | N.D. | N.D. (N.D.) | Type 5 | Multiple sites |
| L-Thyroxine | N.D. | N.D. (53) | Type 4 | Multiple sites |
| Indoxylsulfate | N.D. | 60 (47) | Type 4 | Multiple sites |

[1]Dissociation constants ($K_D$) greater than about 25% of the highest concentration of test ligand are too weak to measure, and are noted N.D. (not determined).
[2]Fluorescent-based $IC_{50}$ values greater than about 50% of the highest concentration of test ligand are too weak to measure, and are noted as N.D. (not determined). The % Displacement represents the percent displacement of the site-specific probe 1,8-ANS at the second highest concentration.
[3]The compound iophenoxate has high binding affinity compared to the protein concentration, thus $IC_{50}$ values require a hill coefficient that is greater than 1 (h = 1.8) and the $IC_{50}$ underestimates the $K_D$. All other compounds were fit with well with h = 1.
[4]Two compounds, ketoprofen and diclofenac, are reported to bind to both sites 1 and 2 on HSA, with higher affinity to site 2, as described in the text.

In Table 2, the values of $K_D$ and $IC_{50}$s are determined from the thermal stability assay and by examination of the fluorescence data. The percent displacement of fluorescence or % Displacement is a measure of the extent or degree that the site-specific probe may be displaced by the binding of a test ligand. The decrease in fluorescence values with increasing compound concentration is used to define the specificity. The values from Table 2 in column 3 show a range of affinity ($IC_{50}$) and an independent value for the percentage of displacement. In general, when the affinity of a test ligand is weaker than half of the highest test concentration, the protein stability is unchanged and thus a binding constant, $K_D$, cannot be determined by the thermal shift assay. Likewise, if the affinity of a test ligand is weaker than half of the highest test concentration, the dye fluorescence does not change and thus an inhibition constant, $IC_{50}$, is not determined by examining the fluorescence.

There are at least five types of ligand-albumin binding or interaction that may be observed using the present methods. As described above, Type 1 is a ligand binding to site I of albumin, whose $K_D$ is approximately equal to $IC_{50}$, or within about 4-fold range, and percent displacement is more than about 70%; Type 2 is a ligand binding to site II, whose $K_D$ is at least about 5-fold lower than $IC_{50}$ and the percent displacement is less than about 20%; Type 3 is a ligand binding to sites I and II of albumin, whose $K_D$ is at least about 4-fold lower than $IC_{50}$ and there is percent displacement is more than about 30%; Type 4 is a ligand that has no or weak binding affinity to either site I or II of albumin, whose $K_D$ and $IC_{50}$ are not measurable for the range of test ligand concentrations being assayed; and Type 5 is a fluorescent compound, which has a dose-dependent increase of fluorescence (i.e. percent displacement is more than 100% or N.D.), and an $IC_{50}$ may not be measurable even though $K_D$ may be determined.

Based on the above definition, the test compounds were categorized into the five different groups. Briefly, Type 1 includes warfarin, phenylbutazone, iophenoxate, sulfadimethoxine, tenoxicam, and quercetin. These compounds have been previously disclosed for their specific binding to site I of albumin. The value of % Displacement of warfarin, phenylbutazone, iophenoxate, sulfadimethoxine and tenoxicam are more than about 70%; and those of quercetin is about 51%. This difference may be due to a measured compound solubility limit several fold less than the second highest test compound concentration for determining the value of % Displacement. Type 2 includes Furosemide and S-Naproxen. This is consistent with previous reports that these compounds bind specifically to the site 2 of albumin. Type 3 includes ketoprofen and diclofenac, indomethacin, tolbutamide, iodopanoate, ibuprofen, carprofen, and flurbiprofen. Ketoprofen and diclofenac are previously disclosed to have affinity to both sites I and II of albumin (Angelakou et al., Europ Pharma Sci. 9: 123-130, 1999; Chamouard et al., Biochemical Pharma 34: 1695-1700, 1985). Type 4 includes salicylate, chlorpropamide, sulfathiazole, valproate, canrenoate, clofibrate, chlorothiazide, bilirubin, octanoate, L-Thyroxine, and indoxylsulfate. These compounds are known to have weak binding affinity to HSA (Kragh-Hansen et al., Biol Pharm Bull 25: 695-704, 2002) and do not have sufficient binding to show an observable interaction with albumin using the present method. Type 5 includes norharmane and L-tryptophan. These have a fluorescent compound effect in the absence or presence of albumin; however, the fluorescence of norharmane or L-tryptophan did not interfere with the thermal shift assay and $K_D$ determination for norharmane. L-Tryptophan is known to be fluorescent and has weak affinity for albumin; thus may also be categorized as Type 4 with fluorescent behavior.

The current method provides additional information when the ligand binding to both sites occurs or when the ligand is a fluorescence compound. Further, the binding properties to both sites I and II may be inferred from a single assay. This indicates that more information may be obtained from the present assay as compared to other methods.

Example 4

To evaluate the bioavailability of a compound in various species, the compound's affinity and specificity to albumins from human, bovine, rat, and mouse were examined. About 50 μg/mL of human, bovine, rat, and mouse albumins, individually, were added to a mixture of about 4 μM 1,8-ANS, about 150 mM NaCl, about 25 mM PIPES, pH 7.2, and about 0.002% Tween®-20. The resulting 1× reaction mixture comprising human serum albumin, bovine serum albumin, rat serum albumin, or mouse serum albumin was used with a panel of compounds in the binding assay.

The compounds and 1× reaction mixture were dispensed, heated, and analyzed as described above and the results of thermal shift assay dissociation constants ($K_D$) are summarized in Table 3.

TABLE 3

The value of dissociation constant ($K_D$) from the binding assay of various albumins with a panel of compounds.

| Test Ligand | Human Albumin ($K_D$, µM) | Bovine Albumin ($K_D$, µM) | Rat Albumin ($K_D$, µM) | Mouse Albumin ($K_D$, µM) |
|---|---|---|---|---|
| Warfarin | 9.4 | 58.0 | 15.7 | 16.6 |
| Phenylbutazone | 5.1 | 10.9 | 29.4 | 14.0 |
| Salicylate | >62.5 | >62.5 | >62.5 | >62.5 |
| Indomethacin | 4.4 | 6.1 | 5.6 | 4.9 |
| Tolbutamide | 24.1 | 30.2 | 25.2 | 75.7 |
| Chlorpropamide | 34.7 | 41.7 | 29.6 | 110 |
| Iophenoxate | 0.044 | 0.066 | 0.048 | 0.05 |
| Sulfadimethoxine | >62.5 | >62.5 | 9.4 | 69.5 |
| Sulfathiazole | >62.5 | >62.5 | >62.5 | >62.5 |
| Furosemide | 16.7 | 49.1 | 24.0 | 29.9 |
| Tenoxicam | 13.0 | >62.5 | 33.8 | >62.5 |
| Valproate | >62.5 | >62.5 | >62.5 | >62.5 |
| Canrenoate | 39.5 | >62.5 | >62.5 | >62.5 |
| Quercetin | >62.5 | 10.9 | >62.5 | >62.5 |
| Clofibrate | >62.5 | >62.5 | >62.5 | >62.5 |
| Ketoprofen | 21.7 | 29.0 | 33.0 | 30.6 |
| Iodopanoate | 0.633 | 1.303 | 0.96 | 0.758 |
| Ibuprofen | 5.3 | 3.5 | 8.6 | 8.5 |
| S-Naproxen | 5.9 | 16.1 | 18.5 | 11.3 |
| Chlorothiazide | >62.5 | >62.5 | >62.5 | >62.5 |
| Diclofenac | 2.6 | 3.9 | 6.1 | 8.7 |
| Carprofen | 2.1 | 2.91 | 1.53 | 1.09 |
| Norharmane | 17.6 | >62.5 | >62.5 | >62.5 |
| Flurbiprofen | 2.1 | 1.882 | 2.932 | 3.79 |
| Bilirubin | 55.7 | 85.4 | >120 | >120 |
| Octanoate | >62.5 | >62.5 | >62.5 | >62.5 |
| L-Tryptophan | >62.5 | >62.5 | >62.5 | >62.5 |
| L-Thyroxine | >62.5 | >62.5 | 43.2 | 4.5 |
| Indoxylsulfate | >62.5 | 35.1 | 11.7 | 1.6 |

During Drug discovery, compound bioavailability and/or pharmacodynamics may not correlate between species. These species-specific differences may be related to differential affinity of these compounds to albumin. This is illustrated in Table 3.

Several compounds show species specific differences in $K_D$ values. For example, warfarin has similar $K_D$ to albumins from human, rat, and mouse; and a higher $K_D$ to bovine serum albumin. This indicates a reduced strength or affinity of binding of warfarin to bovine albumin. Additionally, canrenoate and norharmane each show undetectable binding to albumins from bovine, rat, and mouse; and have a measurable $K_D$ for human albumin within the range of compound concentrations. Sulfadimethoxine has similar $K_D$ or binding affinity to albumins from human, bovine, and mouse; and a lower $K_D$ for binding to rat albumin. Tenoxicam shows similar $K_D$ values for human and rat albumins; and is higher or undetectable for binding to mouse and rat albumins. Similarly, quercetin shows similar $K_D$ values for human and bovine albumins; and is higher or undetectable for binding to rat and mouse albumins. Finally, thyroxine and indoxylsulfate display tight binding affinity to mouse albumin, and about 10- to 15-fold weaker binding to rat albumin. The $K_D$ value of thyroxine was undetectable to human and bovine albumins. The $K_D$ value of indoxylsulfate was about 20-fold less than those of bovine and undetectable to human.

The results indicate that the binding assay with albumins from various species are comparable for many compounds. For example, phenylbutazone, salicylate, indomethacin, tolbutamide, chlorpropamide, iophenoxate, sulfathiazole, furosemide, valproate, clofibrate, ketoprofen, iodopanoate, ibuprofen, naproxen, chlorothiazide, diclofenac, carprofen, norharmane, flurbiprofen, bilirubin, octanoate, and L-tryptophan show thermal shift assay dissociation constants ($K_D$) that are within a factor of 2 of the average across each species. These results indicate that albumin from various species may be used with the method of the present application.

Analysis of fluorescence data as described above for human albumin was also applied to fluorescence data among albumins from various species. Further, the results of Table 3 were consistent with the classification of compound binding behavior that was defined in Table 2.

Example 5

Dansyl-sarcosine is used as a site-specific probe for evaluating the specificity and affinity of compounds to albumin, as it binds to albumin at the site II (Muller et al., J Pharm Pharmacol 46: 300-304, 1994). Dansyl-sarcosine may be prepared by reacting amines with non-fluorescent dansyl chloride. Dansyl chloride may be used to modify the N-terminal amino acid residue of proteins and to prepare fluorescent derivatives of drugs, amino acids, oligonucleotides and proteins for detection by numerous chromatographic methods (Furst et al., J Liquid Chromatography 12: 2733-2733, 1989).

About 50 µg/mL of human albumin is added to a reaction mixture of about 0.5 µM or about 10 µM of dansyl-sarcosine, about 150 mM NaCl, about 25 mM PIPES, pH 7.2, and about 0.002° A Tween®-20. The resulting reaction mixture is used with a panel of compounds for the binding assay as described above in Examples 2 and 3. A change in fluorescence in addition to stabilization of albumin is detected when a compound binds to site II. Also, a compound that binds to site I changes the stability of albumin without affecting the fluorescence.

Example 6

A non-fluorescent molecule iophenoxate is used as a site-specific probe for evaluating the specificity and affinity of compounds to albumin. About 50 µg/mL of human albumin is added to a reaction mixture of about 5 µM or about 10 µM iophenoxate, about 150 mM NaCl, about 25 mM PIPES, pH 7.2, and about 0.002% Tween®-20. In addition, about 50 µg/mL of human albumin is added to a second mixture of about 150 mM NaCl, about 25 mM PIPES, pH 7.2, and about 0.002% Tween®-20. These mixtures are used with a panel of compounds for the binding assay as described above in Examples 2 and 3. The results of the second mixture determine the affinity and the results of the reaction mixture determine the specificity.

Thus, while there have shown and described and pointed out fundamental novel features of the invention as applied to a preferred embodiment thereof, it will be understood that various omissions and substitutions and changes in the form and details of the experimental designs and devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention.

Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A method for determining both the affinity and specificity of a ligand which binds to albumin in a single assay, comprising the steps of:
    a) contacting a reaction mixture comprising a site-specific fluorescent probe and albumin in the presence, and separately in the absence, of said ligand; wherein the concentration of said site-specific fluorescent probe is in the range of about 0.5 µM to about 20 µM, wherein said site-specific fluorescent probe:
        i) increases in fluorescence when bound to albumin, as measured by a spectral reading device;
        ii) binds specifically to a binding site I or a binding site II on said albumin; and
        iii) has a higher affinity for albumin in the denatured state than when said albumin is in its native state;
    and wherein ligand binding to binding site I or binding site II is measured by displacement of the site-specific fluorescent probe by said ligand when it binds to said albumin;
    b) measuring an initial level of fluorescence for the reaction mixture in the presence and separately in the absence of said ligand;
    c) comparing the initial level of fluorescence for the reaction mixture in the presence and the absence of said ligand; whereby differences in the level of the initial fluorescence in the presence or in the absence of said ligand indicates that said ligand does or does not, respectively, bind to said binding site I or binding site II on said albumin;
    d) heating said reaction mixture;
    e) measuring a change in fluorescence of the reaction mixture associated with the thermal unfolding of said albumin, resulting from said heating, in the presence and separately in the absence of said ligand;
    f) generating a thermal unfolding curve from the change of fluorescence measured in (e) for said albumin in the presence and separately in the absence of said ligand as a function of temperature for the reaction mixture;
    g) comparing said thermal unfolding curves for said albumin in the presence and the absence of said ligand generated in (f); whereby differences in the thermal unfolding curves are used to determine the affinity of the ligand which binds to albumin; and
    h) determining both the affinity and specificity of said ligand which binds to albumin by comparing the differences in the thermal unfolding curves in (g) and comparing the differences in the level of the initial fluorescence in (c); thereby determining both the affinity and specificity of said ligand which binds to albumin in a single assay.

2. The method of claim 1, wherein said initial level of fluorescence in step (b) and the change in fluorescence of the reaction mixture associated with the thermal unfolding in step (d) are measured by a plate-based fluorescence reader.

3. The method of claim 1, wherein said albumin is selected from the group consisting of: human serum albumin, bovine serum albumin, rat serum albumin and mouse serum albumin.

4. The method of claim 1, wherein said site-specific fluorescent probe is selected from the group consisting of: 1-anilinonaphtalene-8-sulfonate (1,8-ANS) and dansyl-sarcosine.

5. The method of claim 4, wherein said site-specific fluorescent probe is 1,8-ANS.

6. The method of claim 4, wherein said site-specific fluorescent probe is dansyl-sarcosine.

7. The method of claim 5, wherein a change in the initial level of fluorescence of 1,8-ANS indicates that said ligand binds to said albumin at binding site I.

8. The method of claim 6, wherein a change in the initial level of fluorescence of dansyl-sarcosine indicates that said ligand binds to said albumin at binding site II.

9. The method of claim 1, wherein the concentration of said site-specific fluorescent probe is in the range of about 1.0 µM to about 8 µM.

10. The method of claim 1, wherein the concentration of said site-specific fluorescent probe is in the range of about 2.0 µM to about 4 µM.

* * * * *